(12) United States Patent
McElhaney et al.

(10) Patent No.: US 11,285,294 B2
(45) Date of Patent: Mar. 29, 2022

(54) INTRODUCER WITH SHEATH HAVING A WITHDRAWAL SUPPORT WIRE

(71) Applicant: Cook Medical Technologies LLC, Bloomington, IN (US)

(72) Inventors: Patrick G. McElhaney, Bloomington, IN (US); Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 253 days.

(21) Appl. No.: 16/454,459

(22) Filed: Jun. 27, 2019

(65) Prior Publication Data
US 2020/0054860 A1    Feb. 20, 2020

Related U.S. Application Data

(60) Provisional application No. 62/719,171, filed on Aug. 17, 2018.

(51) Int. Cl.
| | |
|---|---|
| *A61M 25/06* | (2006.01) |
| *A61M 25/00* | (2006.01) |
| *A61M 29/00* | (2006.01) |
| *G05B 19/4155* | (2006.01) |

(Continued)

(52) U.S. Cl.
CPC ...... *A61M 25/005* (2013.01); *A61M 25/0662* (2013.01); *A61M 29/00* (2013.01);
(Continued)

(58) Field of Classification Search
CPC .............. A61M 25/0662; A61M 29/00; A61M 25/005; A61M 2025/0186;
(Continued)

(56) References Cited

U.S. PATENT DOCUMENTS 5,069,674 A * 12/1991 Fearnot ............... A61M 25/005
                                              604/524
5,380,304 A *  1/1995 Parker ............... A61M 25/0012
                                              138/138

(Continued)

OTHER PUBLICATIONS

European Patent Office, European Search Report for Application No. 19189447.6, dated Jan. 20, 2020, Munich, Germany.

*Primary Examiner* — Richard G Louis
(74) *Attorney, Agent, or Firm* — Liell + McNeil

(57) ABSTRACT

An introducer includes a dilator received in a lumen defined by an introducer sheath and including a dilation end extending distally beyond a distal end of the introducer sheath. The introducer sheath includes a flat wire reinforcement having a hollow cylindrical shape sandwiched between an inner PTFE tube and an outer nylon tube. The outer nylon tube includes a distal segment that extends distally beyond the PTFE tube, which extends distally beyond the PTFE tube, which extends distally beyond the flat wire reinforcement. A withdrawal support wire has a distal end attached to a distal end turn of the flat wire reinforcement and extends in a proximal direction in parallel with a longitudinal axis between an outer surface of the nylon tube and an inner surface of the PTFE tube. The withdrawal support wire is configured to be in tension when the sheath is placed in tension to inhibit distal stretch separation breakage.

1 Claim, 2 Drawing Sheets

(51) Int. Cl.
*A61M 25/01* (2006.01)
*A01G 25/16* (2006.01)

(52) U.S. Cl.
CPC ........ G05B 19/4155 (2013.01); *A01G 25/167* (2013.01); *A61M 2025/0186* (2013.01); *A61M 2025/0681* (2013.01); *A61M 2025/0687* (2013.01); *G05B 2219/2625* (2013.01)

(58) Field of Classification Search
CPC ...... A61M 2025/0687; A61M 25/0051; A61M 2025/0681; G05B 19/4155; G05B 2219/2625; A01G 25/167
See application file for complete search history.

(56) References Cited

U.S. PATENT DOCUMENTS

| | | | |
|---|---|---|---|
| 6,013,084 A * | 1/2000 | Ken | A61B 17/12154 606/108 |
| 6,939,337 B2 | 9/2005 | Parker et al. | |
| 7,972,323 B1 | 7/2011 | Bencini et al. | |
| 8,409,169 B1 * | 4/2013 | Moss | A61M 25/0052 604/526 |
| 8,475,431 B2 | 7/2013 | Howat | |
| 8,613,713 B2 | 12/2013 | Delaney | |
| 8,758,231 B2 | 6/2014 | Bunch et al. | |
| 8,864,685 B2 | 10/2014 | Patterson et al. | |
| 8,911,397 B2 | 12/2014 | O'Donnell et al. | |
| 2005/0256452 A1 | 11/2005 | DeMarchi et al. | |
| 2006/0064036 A1 | 3/2006 | Osborne et al. | |
| 2006/0276824 A1 * | 12/2006 | Mitelberg | A61B 17/12113 606/200 |
| 2008/0097293 A1 | 4/2008 | Chin et al. | |
| 2013/0018318 A1 | 1/2013 | Ravichandran et al. | |
| 2013/0238003 A1 | 9/2013 | Fischer et al. | |
| 2013/0289697 A1 | 10/2013 | Baker et al. | |
| 2015/0230953 A1 | 8/2015 | Bar et al. | |
| 2016/0128723 A1 | 5/2016 | Ginn et al. | |

* cited by examiner

INTRODUCER WITH SHEATH HAVING A WITHDRAWAL SUPPORT WIRE

TECHNICAL FIELD

The present disclosure relates generally to introducer sheaths, and more particularly to inclusion of a withdrawal support wire to inhibit separation breakage when the sheath is placed in tension.

BACKGROUND

The Seldinger technique can involve the use of an introducer that provides a valved passageway for passing medical instruments from outside of a patient through the introducer and into the vascular network of the patient. U.S. Pat. No. 5,380,304 describes a flexible, kink-resistant, introducer sheath that has seen considerable success over many years. The '304 introducer sheath includes a flat wire coil sandwiched between an inner PTFE tube and an outer nylon tube. Although this type of introducer sheath has performed magnificently for literally decades, on some rare occasions distal stretch separation breakage among the PTFE tube, the flat wire coil and the outer nylon tube can occur when the introducer sheath is placed in tension, such as when the introducer sheath is being withdrawn from a patient.

The present disclosure is directed toward one or more of the problems set forth above.

SUMMARY

An introducer includes a introducer sheath and a dilator that have a first configuration and a second configuration. The dilator has a dilation end extending distally beyond a distal end of the introducer sheath, and the dilator being positioned in a lumen defined by the introducer sheath, and the dilator extending proximally through a valve at a proximal end of the introducer sheath in the first configuration. The dilator being out of contact with the introducer sheath in the second configuration. The sheath includes a flat wire reinforcement having a hollow cylindrical shape sandwiched between an inner PTFE tube and an outer nylon tube. The outer nylon tube includes a distal segment that extends distally beyond the PTFE tube, which extends distally beyond the flat wire reinforcement. A withdrawal support wire has a distal end attached to a distal end turn of the flat wire reinforcement, and extends in a proximal direction in parallel with a longitudinal axis between an outer surface of the nylon tube and an inner surface of the PTFE tube. The withdrawal support wire being configured to be in tension when the sheath is placed in tension to inhibit distal stretch separation breakage.

DETAILED DESCRIPTION

An introducer sheath according to the present disclosure means a relatively short tube that may be positioned partially within a patient's cardiovascular system and extend outside of the patient to facilitate passage of flexible medical devices into the patients circulatory system. An introducer may be initially be positioned partially in and partially out of a patient using the well known Seldinger technique, where a hollow needle initially penetrates into an artery or vein, and is exchanged with a wire. An introducer, which includes an introducer sheath and a dilator is slid along the wire until a distal end of both the dilator and introducer sheath are positioned in the artery or vein. Thereafter, the wire may be withdrawn and the dilator may be withdrawn leaving the introducer sheath in place. Thereafter, some medical procedure may be performed, such as angioplasty, by passing a balloon catheter through a valve located at a proximal end of the introducer sheath, through a lumen of the introducer sheath and into the patient's cardiovascular system to a treatment location. Those skilled in the art will appreciate that, in some instances, arteries or veins can tend to constrict around an introducer sheath making the withdrawal of the introducer sheath require a greater pulling force.

One class of composite introducer sheaths can occasionally exhibit distal stretch separation breakage when tension in the introducer sheath becomes acute when a practitioner is attempting to withdraw the introducer sheath from a patient after completing a medical procedure. In particular, introducer sheaths made in accordance with co-owned U.S. Pat. No. 5,380,304 include an inner PTFE tube surrounded by a flat wire coil. An outer nylon tube covers that flat wire coil and becomes connected to an outer surface of the PTFE tube between adjacent turns of the flat wire coil. Those skilled in the art will appreciate that the inner PTFE tube helps provide a low friction surface against which medical devices are slid along when being introduced into a patient. The flat wire coil assists in providing reinforcement and inhibits kinking. The outer nylon tube presents a heat formable polyamide material that is advantageously self-leveling for providing a smooth outer surface to the introducer sheath. May be because the different layers (PTFE tube, flat wire coil and nylon tube) have differing elasticities, separation breakage at the distal segment of the introducer sheath can occur on rare occasions. The present disclosure addresses this rare problem by the inclusion of a withdrawal support wire that goes into tension when the introducer sheath is withdrawn from a patient to inhibit the occurrence of distal stretch separation breakage.

Figure 1:
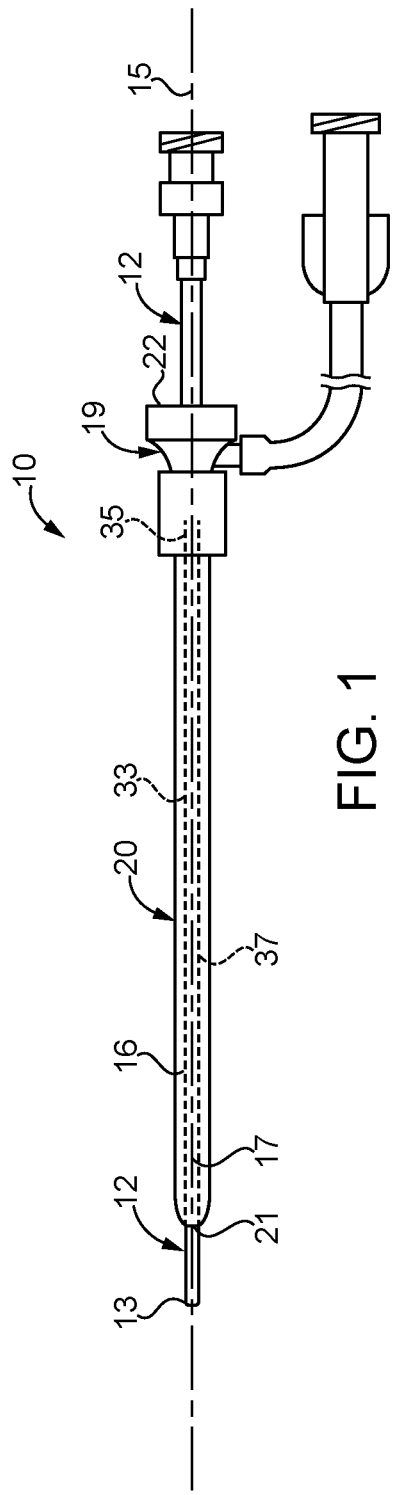
FIG. 1 is a side view of an introducer according to the present disclosure in a first configuration.

Referring initially to FIG. 1, from the outside, an introducer 10 according to the present disclosure may look the same as an introducer manufactured according to the teachings of U.S. Pat. No. 5,380,304, and sold for many years under the FLEXOR trademark. The introducer 10 includes an introducer sheath 20 and a dilator 12 that have a first configuration, as shown, and a second configuration in which the dilator 12 is out of contact with the introducer sheath 20. The dilator 12 has a dilation end 13 that extends distally beyond a distal end 21 of the introducer sheath. The dilator 12, which may be longer than the introducer sheath 20, is positioned in a lumen defined by the introducer sheath.

The dilator 12 extends proximally through a valve 22 at a proximal end of an introducer sheath. Those skilled in the art will recognize that the dilator 12 preferably defines a lumen for receiving a wire guide therethrough for positioning the introducer 10 over a wire guide as previously described.

Figure 2:
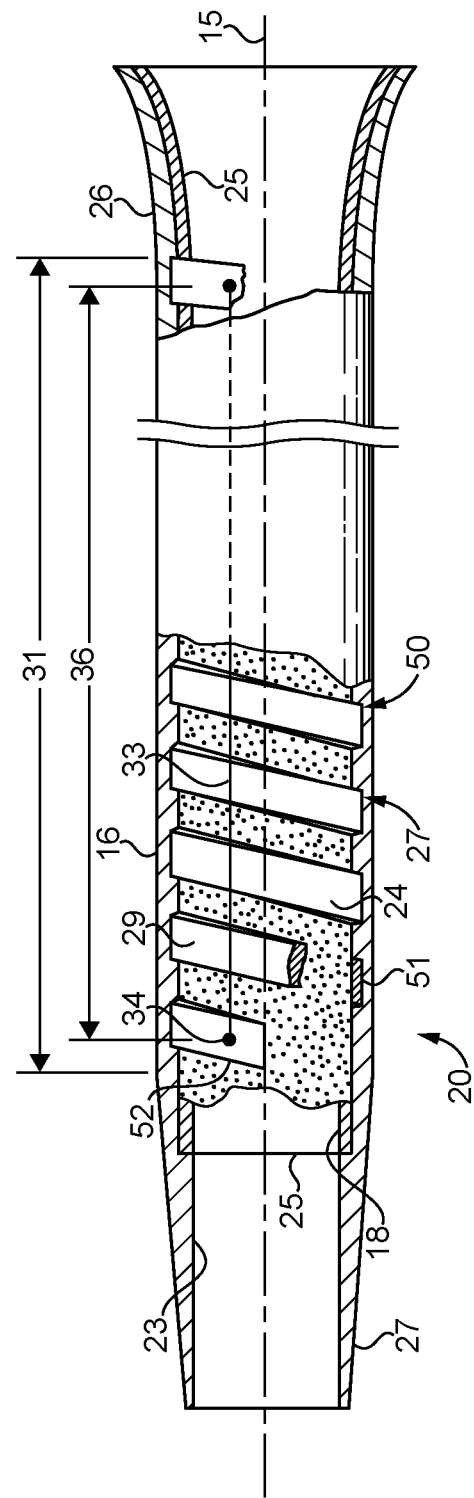
FIG. 2 is a partially sectioned side view of an introducer sheath according to the present disclosure.

Referring now in addition to FIG. 2, introducer sheath 20 includes a flat wire reinforcement 24 which has a hollow cylindrical shape and is sandwiched between an inner PTFE tube 25 and an outer nylon tube 26. The wall of the inner PTFE tube prevents the turns of the flat wire coil 24 from extending into the lumen 23 of the introducer sheath 20. The spacing along longitudinal axis 15 between coil turns may be uniform, and preferably are spaced sufficiently enough that the heat formable nylon connects to a roughened outer surface of the PTFE tube in the spacing between coils. Preferably, the flat wire reinforcement 24 is compression fitted around, and applies a compressive force to, the inner PTFE tube 25. The outer nylon tube 26 includes a distal segment 27, which may include a narrowing tapper in a distal direction, that extends distally beyond a distal end of the PTFE tube 25, which extends distally beyond the distal end of the flat wire reinforcement 24. A withdrawal support wire 33 has a distal end 34 attached to a distal end turn 52 of the flat wire reinforcement 24, such as by welding. The withdrawal support wire 33 extends in a proximal direction in parallel with the longitudinal axis 15 and is located entirely between an outer surface 16 of the nylon tube and an inner surface 18 of the PTFE tube 25. In the example of FIG. 2, the withdrawal support wire is attached at its distal end 34 to the distal end turn 52 of the flat wire reinforcement 24, and attached at its proximal end to the proximal end turn of a flat wire coil such that the flat wire reinforcement 24 has a length 31 that is longer than a length 36 of the withdrawal support wire 33. In this example, the withdrawal support wire 33 is in contact with an outer surface 29 of the flat wire reinforcement 24. The portion of the withdrawal support wire 33 extending in the proximal direction away from the distal end turn 52 may be attached to one or more of the other turns of the flat wire reinforcement 24, or may have no further attachment to the flat wire reinforcement 24 without departing from the present disclosure. For instance, and as shown with hidden lines in FIG. 1, the withdrawal support wire may have a proximal end connected to a hub 19, which may include a valve 22, mounted at a proximal end of introducer sheath 20. Furthermore, although FIG. 2 shows a single withdrawal support wire 33, a introducer sheath 20 having two or more withdrawal support wires would also fall within the intended scope of the present disclosure. For instance, FIG. 1 shows a first withdrawal support wire 33 and a second withdrawal support wire 37 located on opposite sides of a plane that extends into and out of the page and includes longitudinal axis 15. The introducer sheath 20 shown in FIG. 2 has a flared proximal end for attachment to a hub 19 as shown in FIG. 1 in a manner well known in the art.

Figure 3:
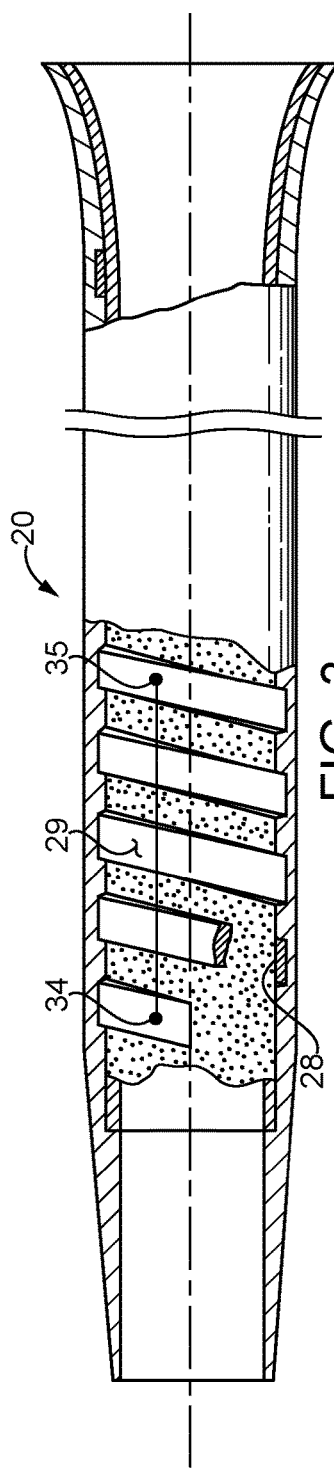
FIG. 3 is a partially sectioned side view of an introducer sheath according to another embodiment of the present disclosure.

Referring now in additional to FIG. 3, an alternative structure according to the present disclosure includes the withdrawal support wire 33 alternately in contact with an external surface 29 of the flat wire reinforcement 24 and an internal surface 28 of the flat wire reinforcement 24 so as to alternately pass over and under successive turns of the flat wire reinforcement 24. Although the present disclosure preferably teaches that the withdrawal support wire be manufactured from a suitable medical grade metallic alloy, other materials, such as suture material, that can support tension forces would also fall within the intended scope of the present disclosure. Preferably, the cross sectional area of the withdrawal support wire 33 is small and thus has a small to negligible effect on the surface features of the introducer sheath. Withdrawal support wire could have a variety of cross-sectional shapes without departing from the present disclosure. These include round, flat rectangle or any shape between. Thus, the withdrawal support wire 33 may be preferably welded to the flat wire reinforcement 24, but other attachment strategies could also fall within the intended scope of the present disclosure. Although not necessary, the withdrawal support wire 33 may be welded to at least one other turn of the flat wire reinforcement 24 other than the distal end turn 52 as shown in both FIGS. 2 and 3. In the embodiments of FIGS. 1-3, the flat wire reinforcement 24 is in the form of a coil 50 formed from flat wire 51. In the context of the present disclosure, the term "flat wire" means a cross section with a rectangular shape, with the long sides of the rectangle forming the interior surface 28 and the external surface 29 of the flat wire reinforcement 24, respectively.

Figure 4:
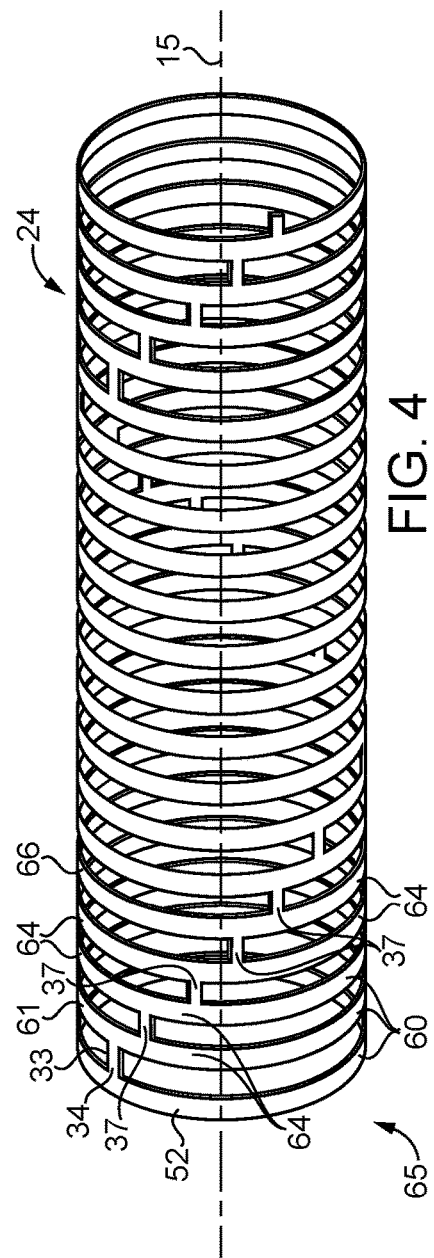
FIG. 4 is a perspective side schematic view of a flat wire reinforcement for a introducer sheath according to another aspect of the present disclosure.
Figure 5:
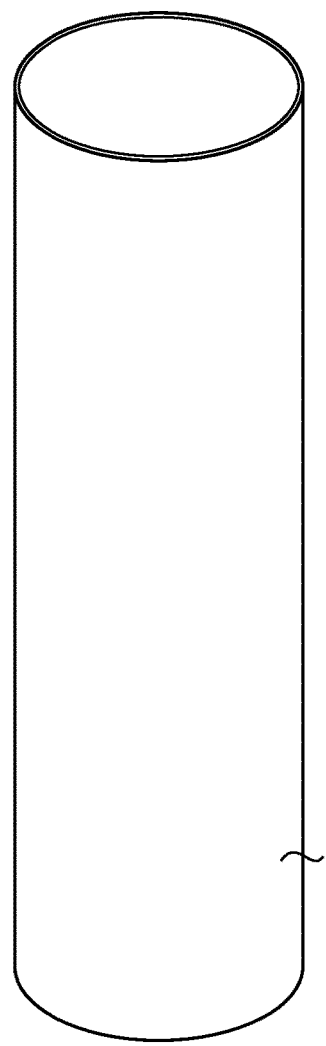
FIG. 5 is a perspective side view of a thin walled metallic tube from which the flat wire reinforcement of FIG. 4 is cut.
Figure 6:
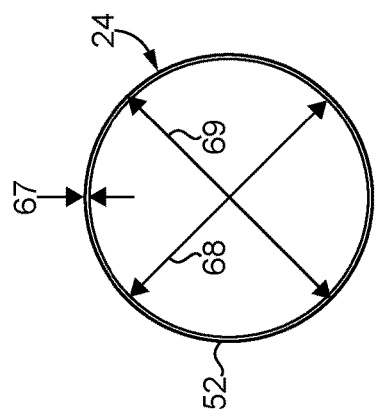
FIG. 6 is an end view of the flat wire reinforcement of FIG. 4.

Referring now in additional to FIGS. 4-6, a flat wire reinforcement 24 according to the present disclosure can have a structure different from the coil 50 of flat wire 51 of the earlier embodiments. In particular, a flat wire reinforcement 24 according to the present disclosure can comprise a plurality of flat wire hoops 60 that each lay in spaced apart planes that are oriented perpendicular to the longitudinal axis 15 as shown in FIG. 4. This structure may be cut from a single solid piece of thin walled tubing 70, as shown in FIG. 5 such as by being laser cut in the manner of a cannula cut stent known in the art. In one version, the withdrawal support wire 33 is located entirely between the distal end turn 52 and the next proximal turn 61, and may find its origin as a portion of the thin walled tube 70 such that no welding or other attachment strategy is necessary. In other words, the withdrawal support wire 33 and the flat wire reinforcement 24 may be portions of an integral one piece component 66 that is cut away from the thin walled tube 70 shown in FIG. 5. Preferably, the integral one-piece component part 66 has a uniform wall thickness 67, may be with a thickness similar to the thickness of the flat wire of the coil 50 of the earlier embodiment. In the embodiment of FIG. 4, the flat wire reinforcement 24 includes a plurality of withdrawal support wires 33 and 37. Each of the withdrawal support wires 33, 37 is located entirely between two successive turns 64 of the flat wire reinforcement 24. In fact, the plurality of withdrawal support wires 33, 37 may be arranged in a helical pattern 65 about the longitudinal axis 15 as shown in FIG. 4 in order to minimize the effect of the withdrawal support wires 33, 37 on the flexibility of the finished introducer sheath 20. Other patterns of distributing withdrawal support wires, besides helical, would also fall within the intended scope of this disclosure. For instance, a repeating pattern of top/bottom/left/right might provide different but desirable properties. When the flat wire reinforcement 24 is cut from a thin walled tube 70 as shown in FIGS. 4-6, the flat wire reinforcement(s) 33, 37 is located entirely between an inner diameter 68 and an outer diameter 69 of the flat wire reinforcement 24. Thus, those skilled in the art will recognize that when the withdrawal support wire 33, 37 and the flat wire reinforcement 24 are cut from the same thin walled tube 70, the withdrawal support wire 33, 37 requires no separate attachment strategy and does not add to the wall thickness at any location of the finished introducer sheath 20.

INDUSTRIAL APPLICABILITY

The present disclosure finds application in inhibiting distal stretch separation breakage in composite introducer sheaths. The present disclosure finds specific application in introducer sheaths that include a flat wire reinforcement sandwiched between a PTFE inner tube and a nylon outer tube.

When the introducer sheath 20 is placed in tension, such as when being withdrawn from a patient's vascular system, the withdrawal support wire 33 is positioned and designed to carry tension that might otherwise cause distal stretch separation breakage among the distal end coil 52 and the flanking PTFE and nylon tubes, but otherwise have no substantial influence on the performance of the introducer 10 when being placed in a patient or when medical devices are slid therethrough to perform medical procedures in a manner known in the art. In other words, the withdrawal support wire may be sized, designed and positioned to support tension levels that might otherwise be associated with the distal stretch separation breakage issue identified previously.

The present description is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended claims.

What is claimed is:

1. An introducer comprising:
   a introducer sheath and a dilator that have a first configuration and a second configuration;
   the dilator has a dilation end extending distally beyond a distal end of the introducer sheath and the dilator being positioned in a lumen defined by the introducer sheath, and the dilator extending proximally through a valve at a proximal end of the introducer sheath in the first configuration;
   the dilator being out of contact with the introducer sheath in the second configuration;
   the introducer sheath includes a flat wire reinforcement having a hollow cylindrical shape sandwiched between an inner PTFE tube and an outer nylon tube;
   the outer nylon tube including a distal segment that extends distally beyond the PTFE tube, which extends distally beyond the flat wire reinforcement;
   a withdrawal support wire with a distal end attached to a distal end turn of the flat wire reinforcement and extending in a proximal direction in parallel with a longitudinal axis between an outer surface of the nylon tube and an inner surface of the PTFE tube; and
   the withdrawal support wire being configured to be in tension when the introducer sheath is placed in tension, to inhibit distal stretch separation breakage;
   wherein a proximal end of the withdrawal support is affixed to a hub at the proximal end of the dilator such that the proximal end of the withdrawal support does not move with respect to the hub.

* * * * *

UNITED STATES PATENT AND TRADEMARK OFFICE
CERTIFICATE OF CORRECTION

PATENT NO. : 11,285,294 B2
APPLICATION NO. : 16/454459
DATED : March 29, 2022
INVENTOR(S) : Patrick G. McElhaney and Thomas A. Osborne It is certified that error appears in the above-identified patent and that said Letters Patent is hereby corrected as shown below:

On the Title Page

Under the section entitled "Related U.S. Application Data", item (60) should read as follows:
Provisional application No. 62/719,191, filed on Aug. 17, 2018

Signed and Sealed this
Twenty-fifth Day of October, 2022

Katherine Kelly Vidal
*Director of the United States Patent and Trademark Office*